United States Patent [19]

Pilgram et al.

[11] Patent Number: 4,589,913
[45] Date of Patent: May 20, 1986

[54] ALKOXYCARBONYLTHIOAMINO-SUBSTITUTED TRIAZINONES

[75] Inventors: Kurt H. Pilgram; Gene A. Bozarth, both of Modesto, Calif.

[73] Assignee: Shell Oil Company, Houston, Tex.

[21] Appl. No.: 715,790

[22] Filed: Mar. 25, 1985

[51] Int. Cl.$^4$ .................. A01N 43/707; C07D 253/06
[52] U.S. Cl. ........................................ 71/93; 544/182
[58] Field of Search ............................ 544/182; 71/93

[56] References Cited

U.S. PATENT DOCUMENTS 3,671,523  6/1972  Westphal et al. ................... 544/182
4,405,779  9/1983  Wiley ................................. 544/182

Primary Examiner—John M. Ford

[57] ABSTRACT

Certain 4-(alkoxycarbonylthioamino)-6-alkyl-3-methylthio-1,2,4-triazin-5(4H)-ones, and their use for controlling the growth of unwanted plants.

2 Claims, No Drawings

ALKOXYCARBONYLTHIOAMINO-SUBSTITUTED TRIAZINONES

BACKGROUND OF THE INVENTION 1,2,4-triazin-5(4H)-ones substituted at the 4-position by an amino moiety, at the 6-position by an alkyl moiety and at the 3-position by an alkylthio moiety form a well-known class of herbicides, claimed in U.S. Pat. No. 3,671,523. One species, 4-amino-6-tert-butyl-3-methylthio-1,2,4-triazin-5(4H)-one, commonly known as metribuzin, is a commerical product, marketed under the trademark "Sencor".

However, such compounds are very soluble in water, and thus susceptible to being leached from soil by rainfall or irrigation water.

DESCRIPTION OF THE INVENTION

It has now been found that if the 4-amino moiety of a 4-amino-6-alkyl-3-methylthio-1,2,4-triazin-5(4H)-one is derivatized to form an alkoxycarbonylthioamino moiety, the resulting compounds are much less soluble in water, yet are equally effective for controlling the growth of unwanted plants. Further, the derivatives are much more soluble in organic solvents that are suitable for use in emulsible concentrate formulations, thus being more adapted to formulation in such a mode.

These new derivatives are described by the formula:

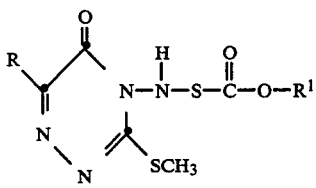

wherein R is straight-chain or branched-chain alkyl of three to five carbon atoms or cycloalkyl of three or four carbon atoms, and $R^1$ is straight-chain or branched-chain alkyl of one to eight carbon atoms.

Because of their biological and physical properties, a preferred subclass of these compounds consists of those wherein R is tertiary-butyl and $R^1$ contains from one to four carbon atoms.

Compounds of formula I can be prepared by treating the appropriate triazinone of the formula

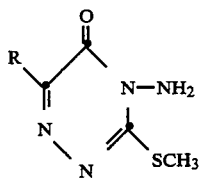

with the appropriate $R^1$-oxycarbonylsulfenyl chloride

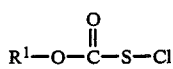

in the presence of an inert solvent and in the presence of a nitrogen base as hydrogen halide acceptor.

Treatment of the triazinone with the sulfenyl halide is conveniently conducted by adding the halide to a stirred solution of the triazinone in a solvent at a temperature of about 0°–20° C., slowly adding a tertiary amine thereto, then stirring the reaction mixture at room temperature until the reaction is complete. Suitable solvents are haloalkenes or aromatic hydrocarbons. A preferred nitrogen base is N,N-diisopropyl-N-ethylamine. Conduct of the treatment is particular instances, and illustration of the work-up of the reaction mixtures, and isolation of the products, effected by conventional techniques, are illustrated in the examples hereafter.

The triazinone precursors (of Formula II) and methods for their preparation are disclosed in U.S. Pat. No. 3,671,523.

The sulfenyl halides of Formula III and methods for their preparation are known: G. Zumach and E. Kühle, Angewandte Chemie, International Edition, 9, 54–63 (1970); H. Böhme and M. Clement, Liebig's Annalen der Chemie, 576, 61–69 (1951); H. Böhme and H. D. Steudel, Liebig's Annalen der Chemie, 730, 121–132 (1969).

The preparation, isolation and physical properties of typical individual species of the compounds of Formula I, in particular instances, are described in the following examples. In each case, the identity of the product, and each of any intermediate involved, was confirmed by appropriate chemical and spectral analyses.

EXAMPLE 1

6-(tert-butyl)-4-(methoxycarbonylthioamino)-3-(methylthio)-1,2,4-triazin-5(4H)-one (1)

19.8 g of anhydrous methanol was added drop-by-drop to stirred 81.3 g of (chlorothio)formyl chloride at 30°–60° C. The mixture was stirred for 20 minutes at room temperature, then distilled at 95 Torr. pressure in a Vigreaux column to give (methoxycarbonyl)sulfenyl chloride, (1A) as a fraction boiling at 75°–79° C. (pot), 60°–72° C. (head).

7.6 g of 1A was mixed with 10.7 g of metribuzin and 200 ml of methylene chloride. The mixture was cooled to 0° C. and 7.7 g of N,N-diisopropyl-N-ethylamine was added drop-by-drop to the stirred mixture over 1.5 hours. Then the mixture was stirred at 0° C. for 2 hours, at room temperature for 2 days, washed with water and dried (MgSO₄), and the solvent was evaporated. The residue was chromatographed over a column of silica gel, using a 2:15:33 v:v:v mixture of tetrahydrofuran, ethyl acetate and hexane as eluent. Two fractions were obtained, 1 being the second fraction with tlc Rf=0.60, taken in a 1:1:2 v:v:v mixture of tetrahydrofuran, ethyl acetate and hexane, as an amber syrup.

EXAMPLES 2–4

6-(tert-butyl)-4-(ethoxycarbonylthioamino)-3-methylthio)-1,2,4-triazin-5(4H)-one (2)

6-(tert-butyl)-4-(n-propoxycarbonylthioamino)-3-methylthio)-1,2,4-triazin-5(4H)-one (3)

6-(tert-butyl)-4-(n-butoxycarbonylthioamino)-3-(methylthio)-1,2,4-triazin-5(4H)-one (4)

These three species were prepared, as amber syrups, by treating metribuzin with (ethoxycarbonyl)sulfenyl chloride, (n-propoxycarbonyl)sulfenyl chloride and (n-butoxycarbonyl)sulfenyl chloride, respectively, by the procedure described in Example 1 for preparing 1 from 1A, each of the chlorides having been prepared from the appropriate alcohol by the procedure described in Example 1 for the preparation of 1A from methanol.

EXAMPLE 5

6-(tert-butyl)-4-(sec-butoxycarbonylthioamino)-3-(methylthio)-1,2,4-triazin-5(4H)-one (5)

94.5 g of potassium was added in portions to 1500 ml of 2-butanol under nitrogen, the temperature of the mixture being allowed to rise from room temperature to 85° C. The resulting solution was cooled to 15° C. and 162 g of carbonyl sulfide was added, with stirring. The resulting mixture was stirred at room temperature for 2 hours, diluted with one liter of ether and filtered. The solid thus obtained was washed with ether and dried to give the potassium salt of the 0-(sec-butyl)ester of thiocarbonic acid (5A), as an off-white solid, m.p.: 230°–240° C. (with decomposition).

188.4 g of acetyl chloride was added drop-by-drop over a 2-hour period to a stirred suspension of 395 g of 5A in 1500 ml of methylene dichloride at −15° C. The resulting mixture was stirred at −15° C. to −5° C. for 2 hours, at 0° C. for 3 hours and at room temperature for 18 hours. The mixture was filtered and the filtrate was concentrated at about 30 Torr. and 30° C., to give thiocarbonic acid, anhydrosulfide with thioacetic acid, 0-(sec-butyl)ester (5B), as a pale yellow oil.

A solution of 188 g of chlorine in 3 liters of cold methylene chloride was added drop-by-drop (2.5 hours) to a mixture of 372 g of 5B and 1 liter of methylene chloride at −20° C. to 10° C. The resulting mixture was held at room temperature for 18 hours, then concentrated at 30 Torr. and 25° C. The residue was vacuum distilled to give ((sec-butoxy)carbonyl)sulfenyl chloride (5C), as a fraction (light yellow) collected at 45°–50° C., 5 Torr.

5 was prepared, as an amber syrup, by treating metribuzin with 5C according to the procedures described for preparing 1 from 1A and 1B, Example 1.

EXAMPLE 6

6-(tert-butyl)-4-(isopropoxycarbonylthioamino)-3-(methylthio)-1,2,4-triazin-5(4H)-one (6)

6 was prepared, as an amber syrup, by treating metribuzin with (isopropoxycarbonyl)sulfenyl chloride (6A), according to the procedure described in Example 1 for preparing 1 from 1A. 6A was prepared from 2-propanol according to the procedure described in Example 5 for preparing 5C from 2-butanol, except using sodium rather than potassium.

All of these derivatives were much less soluble in water, and much more soluble in organic solvents than were their respective precursor triazinones.

Compounds of Formula I have been found to adversely affect the growth of plants, many of which are commonly considered as weeds, and therefore to be useful for controlling the growth of such unwanted plants.

Accordingly, the invention includes a method of combatting unwanted plants which comprises applying to the locus an effective amount of a compound of Formula I. In cases where it is desired to control weeds in crop plantings, it is of course preferable to employ the lowest dosage that will control the weeds, for this will minimize any possible deleterious effect of the compound upon the crop plants.

For application, the compound of Formula I ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3-10% by weight of a dispersing agent, 2-15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100 BS mesh (1.676-0.152 mm), and may be manufactured by agglomeration or impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3-7% by weight of a blend of surfactants, which act as wetting, dispersing, suspending and binding agents, and may contain up to 3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

Primary Tests

In the following examples, the species of plants that were tested were:
Barnyardgrass (watergrass)—*Echinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Velvetleaf—*Abutilon theophrasti*
Garden cress—*Lepidium sativum*
Johnson grass—*Sorghum halepense*
Morningglory—*Impomoea purpurea* L. (Roth)

Test Procedures

The preemergence (soil) herbicidal activity of compounds of Formula I was evaluated by planting seeds of barnyardgrass, garden cress, downy brome, velvetleaf, yellow foxtail, and morniglory in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of Formula I was evaluated by spraying 10-day-old large crabgrass plants, 13-day-old pigweed plants, 6-day-old Johnsongrass plants, 9-day-old velvetleaf plants, 9-day-old yellow foxtail plants and 5-day-old morningglory plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, when the effect of the test compound was evaluated visually, the results being rated on the 0 to 9 scale described above.

The results of the tests are summarized in Table I.

TABLE I

| | HERBICIDAL ACTIVITY | | | | | | | | | | | |
|---|---|---|---|---|---|---|---|---|---|---|---|---|
| | Preemergence | | | | | | Postemergence | | | | | |
| Compound | Barnyard-grass | Garden Cress | Downy Brome | Velvet-leaf | Yellow Foxtail | Morning-glory | Crab-grass | Pig-weed | Johnson-grass | Velvet-leaf | Yellow Foxtail | Morning-glory |
| 1 | 9 | 9 | 9 | 9 | 8 | 6 | 9 | 9 | 6 | 9 | 8 | 2 |
| 2 | 9 | 9 | 8 | 8 | 8 | 6 | 9 | 9 | 3 | 9 | 6 | 3 |
| 3 | 9 | 9 | 9 | 9 | 9 | 6 | 8 | 9 | 2 | 9 | 2 | 3 |
| 4 | 9 | 9 | 9 | 9 | 9 | 6 | 6 | 8 | 2 | 6 | 8 | 2 |
| 5 | 9 | 9 | 7 | 8 | 8 | 4 | 9 | 9 | 6 | 8 | 8 | 4 |
| 6 | 9 | 9 | 9 | 9 | 8 | 9 | 9 | 9 | 3 | 9 | 9 | 5 |

We claim:

1. A compound of the formula:

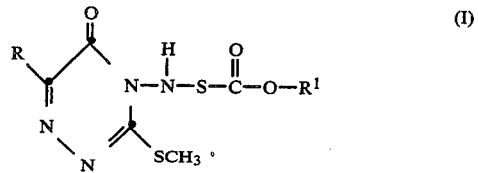

wherein R is straight-chain or branched-chain alkyl of three to five carbon atoms or cycloalkyl of three or four carbon atoms, and $R^1$ is straight-chain or branched-chain alkyl of one to eight carbon atoms.

2. A compound according to claim 1 wherein R is tertiarybutyl and $R^1$ contains from one to four carbon atoms.

* * * * *